US00PP21134P2

(12) United States Plant Patent
Klaver

(10) Patent No.: US PP21,134 P2
(45) Date of Patent: Jun. 29, 2010

(54) ***ZANTEDESCHIA* PLANT NAMED 'FLAMINGO'**

(50) Latin Name: *Zantedeschia aethiopica*
Varietal Denomination: Flamingo

(75) Inventor: Theo C. M. Klaver, Heerhugowaard (NL)

(73) Assignee: Firma Gebroeders Klaver v.o.f., Heerhugowaard (NL)

( * ) Notice: Subject to any disclaimer, the term of this patent is extended or adjusted under 35 U.S.C. 154(b) by 0 days.

(21) Appl. No.: 12/383,844

(22) Filed: Mar. 27, 2009

(51) Int. Cl.
*A01H 5/00* (2006.01)

(52) U.S. Cl. ..... Plt./490

(58) Field of Classification Search ..... Plt./490
See application file for complete search history.

*Primary Examiner*—Annette H Para
(74) *Attorney, Agent, or Firm*—C. A. Whealy

(57) ABSTRACT

A new and distinct cultivar of *Zantedeschia* plant named 'Flamingo', characterized by its upright plant habit; glossy medium green-colored leaves; large pink-colored spathes that are positioned above and beyond the foliage on erect scapes; and good inflorescence longevity.

2 Drawing Sheets

Botanical designation: *Zantedeschia aethiopica.*
Cultivar denomination: 'FLAMINGO'.

BACKGROUND OF THE INVENTION

The present invention relates to a new and distinct cultivar of *Zantedeschia* plant, botanically known as *Zantedeschia aethiopica* and hereinafter referred to by the name 'Flamingo'.

The new *Zantedeschia* plant is a product of a controlled breeding program conducted by the Inventor in Heerhugowaard, The Netherlands. The objective of the breeding program is to create new *Zantedeschias* that have unique and attractive inflorescence coloration.

The new *Zantedeschia* plant originated from an open-pollination made by the Inventor in August, 2005, in Heerhugowaard, The Netherlands of *Zantedeschia aethiopica* 'Pink Mist', not patented, as the female, or seed, parent with an unknown selection of *Zantedeschia aethiopica,* as the male, or pollen, parent. The new *Zantedeschia* was discovered and selected by the Inventor as a single flowering plant within the progeny of the stated open-pollination in a controlled greenhouse environment in Heerhugowaard, The Netherlands in August, 2006.

Asexual reproduction of the new *Zantedeschia* plant by tissue culture in a controlled environment in Heerhugowaard, The Netherlands since October, 2007 has shown that the unique features of this new *Zantedeschia* plant are stable and reproduced true to type in successive generations of asexual reproduction.

SUMMARY OF THE INVENTION

Plants of the new *Zantedeschia* have not been observed under all possible environmental conditions. The phenotype may vary somewhat with variations in environment such as temperature and light intensity, without, however, any variance in genotype.

The following traits have been repeatedly observed and are determined to be the unique characteristics of 'Flamingo'. These characteristics in combination distinguish 'Flamingo' as a new and distinct cultivar of *Zantedeschia:*

1. Upright plant habit.
2. Glossy medium green-colored leaves.
3. Large pink-colored spathes that are positioned above and beyond the foliage on erect scapes.
4. Good inflorescence longevity.

Plants of the new *Zantedeschia* differ from plants of the female parent, 'Pink Mist', in the following characteristics:

1. Flowers of plants of the new *Zantedeschia* are not as open as flowers of plants of 'Pink Mist'.
2. Plants of the new *Zantedeschia* and 'Pink Mist' differ in spathe color as plants of 'Pink Mist' have lighter pink-colored spathes.

Plants of the new *Zantedeschia* can also be compared to plants of *Zantedeschia aethiopica* 'Highwood', not patented. In side-by-side comparisons conducted in Heerhugowaard, The Netherlands, plants of the new *Zantedeschia* differed from plants of 'Highwood' primarily in spathe color as plants of 'Highwood' had white-colored spathes.

BRIEF DESCRIPTION OF THE PHOTOGRAPHS

The accompanying photographs illustrate the overall appearance of the new *Zantedeschia* plant. These photographs show the colors as true as it is reasonably possible to obtain in colored reproductions of this type. Colors in the photographs may differ slightly from the color values cited in the detailed botanical description which accurately describe the colors of the new *Zantedeschia.*

The photograph on the first sheet is a side perspective view of a typical plant of 'Flamingo' grown in a container.

The photograph at the top of the second sheet is a close-up view of a typical inflorescence of 'Flamingo'.

The photograph at the bottom of the second sheet is a close-up view of a typical leaf of 'Flamingo'.

DETAILED BOTANICAL DESCRIPTION

The aforementioned photographs and following observations and measurements describe plants grown in 17-cm containers in Heerhugowaard, The Netherlands during the winter in a glass-covered greenhouse. Plants were grown under conditions and practices which approximate those generally used in commercial *Zantedeschia* production. During the production of the plants, day temperatures averaged 15° C. and night temperatures averaged 12° C. Plants were one year old when the photographs and the detailed description were taken. In the following description, color references are made to The Royal Horticultural Society Colour Chart, 2001 Edition, except where general terms of ordinary dictionary significance are used.

Botanical classification: *Zantedeschia aethiopica* 'Flamingo'.

Parentage:

*Female, or seed, parent.*—*Zantedeschia aethiopica* 'Pink Mist', not patented.

*Male, or pollen, parent.*—Unknown selection of *Zantedeschia aethiopica,* not patented.

Propagation:

*Type.*—By tissue culture.

*Time to initiate roots.*—About two to four days at 12° C. to 15° C.

*Time to produce a rooted young plant.*—About 70 to 90 days at 19° C.

*Root description.*—Thick, fibrous; white in color.

*Rooting habit.*—Moderately branching, moderately dense.

Plant description:

*Plant shape.*—Upright plant habit; narrow inverted triangle.

*Growth habit.*—Basally clumping; moderately vigorous to vigorous growth habit; about 15 stems develop per plant.

*Plant height, from soil level to top of leaf plane.*—About 65.9 cm.

*Plant height, from soil level to top of inflorescences.*—About 79.9 cm.

*Plant diameter or spread.*—About 59.1 cm.

*Foliage description.*—Arrangement: Alternate, basal; simple. Length: About 27.9 cm. Width: About 12.8 cm. Shape: Cordate to sagittate. Apex: Aristate. Base: Hastate to sagittate. Margin: Entire, undulate. Texture, upper and lower surfaces: Smooth, glabrous; slightly leathery. Luster, upper and lower surfaces: Glossy. Venation pattern: Pinnate. Color: Developing leaves, upper surface: Close to 137A. Developing leaves, lower surface: Close to 137B. Fully expanded leaves, upper surface: Close to N137B; venation, close to 143A. Fully expanded leaves, lower surface: Close to 146A to 146B; venation, close to 143B to 143C. Petiole: Length: About 44.2 cm. Diameter, distal: About 1.1 cm. Diameter, proximal: About 1.9 cm. Texture, upper and lower surfaces: Smooth, glabrous. Luster, upper and lower surfaces: Moderately glossy. Color, upper and lower surfaces: Close to 143A to 143B; towards the base, close to 144A to 144B. Wing length: About 22 cm. Wing diameter: About 9 mm. Wing color: Close to 144A; towards the base, close to 144B to 144C.

Inflorescence description:

*Inflorescence arrangement.*—Spathes with spadices held above and beyond the foliage on erect scapes; flowering structures arising from leaf axils; spathes, cupped; spadices, columnar and tapering towards the apex.

*Fragrance.*—None detected.

*Flowering season.*—In The Netherlands, flowering is intermittent from January to July; plants begin flowering about 4.5 months after planting.

*Quantity of inflorescences per plant.*—During the flowering season, typically about 15 inflorescences develop per plant.

*Inflorescence longevity.*—Inflorescences last about 4 to 4.5 weeks on the plant and about 2 to 2.5 weeks as a cut flower; inflorescences persistent.

*Spathe.*—Length: About 10.1 cm. Width: About 11 cm. Shape: Broadly ovate; cupped. Apex: Mucronate. Base: Attenuate. Margin: Entire; revolute; slightly undulate. Texture, upper and lower surfaces: Smooth, glabrous; leathery. Color: When developing and fully expanded, front surface: Close to 36B; towards the margins and apex, close to 27D. When developing and fully expanded, rear surface: Close to 36B; towards the margins and apex, close to 36C to 36D; towards the base, close to 143B to 143C.

*Spadix.*—Length: About 8 cm. Diameter: About 1.1 cm. Shape: Columnar, tapering towards the apex; apex, obtuse; base, obtuse; cross-section, rounded. Color: Immature: Close to 22C to 22D. Mature: Close to 15B to 15C. Flowers, female: Quantity per spadix: About 80. Shape: Rounded. Height: About 2 mm. Diameter: About 4 mm. Stigma color: Close to 150D. Ovary color: Close to 150D. Flowers, male: Quantity per spadix: About 700. Shape: Irregularly oblong. Height: Less than 0.5 mm. Diameter: About 1 mm. Anther color: Close to 15B to 15C. Pollen amount: Moderate to abundant. Pollen color: Close to 11D.

*Scape.*—Length: About 72.5 cm. Diameter: About 2.3 mm. Strength: Moderately strong. Aspect: About 5° from vertical. Color: Close to 144A; towards the base, close to 144C to 144D.

*Seed and fruit.*—Seed and fruit development has not been observed on plants of the new *Zantedeschia.*

Disease/pest resistance: Plants of the new *Zantedeschia* have not been observed to be resistant to pathogens or pests common to *Zantedeschia.*

Temperature tolerance: Plants of the new *Zantedeschia* have been observed to be tolerant to temperatures ranging from about 0° C. to about 30° C.

It is claimed;

1. A new and distinct *Zantedeschia* plant named 'Flamingo' as illustrated and described.

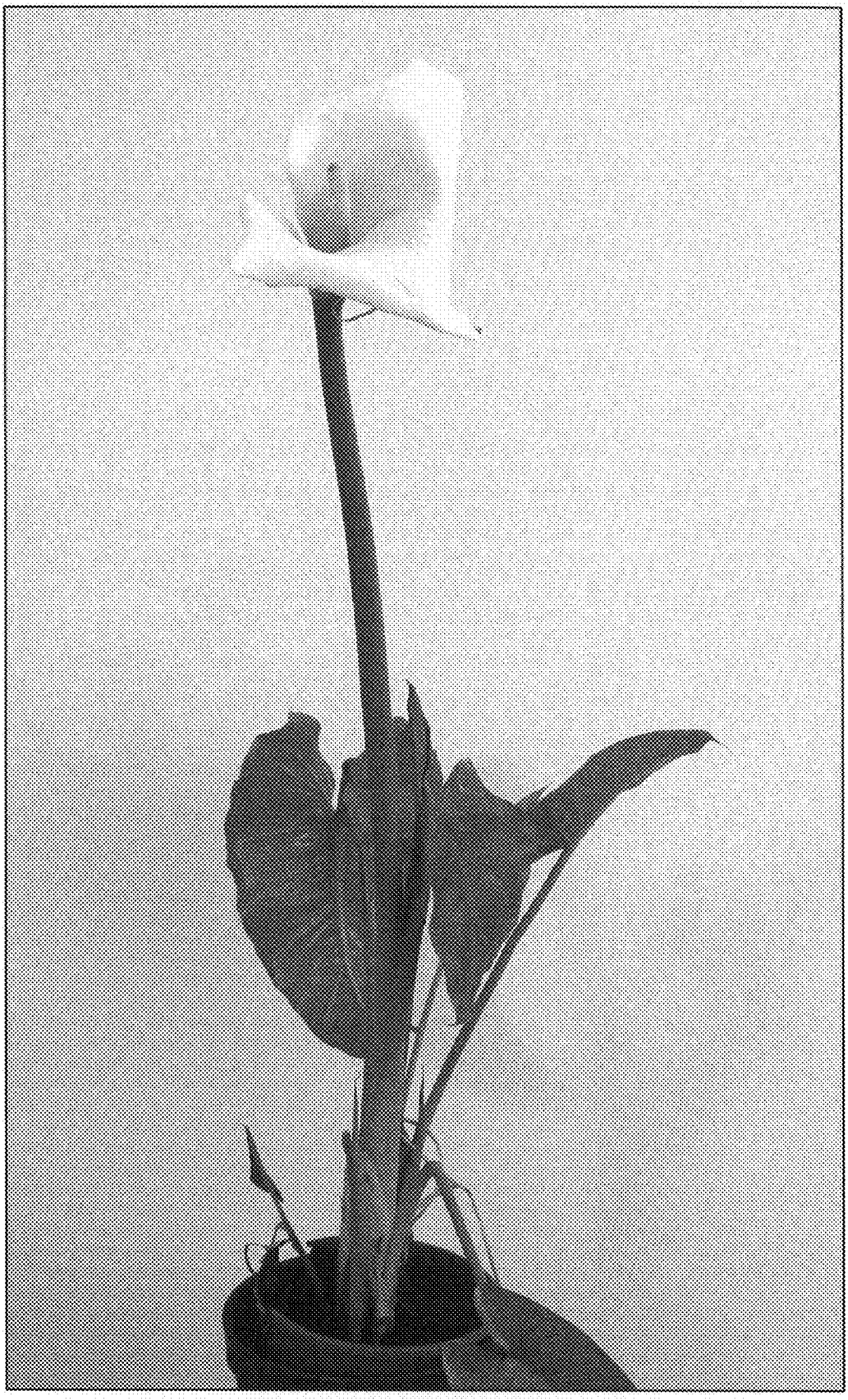

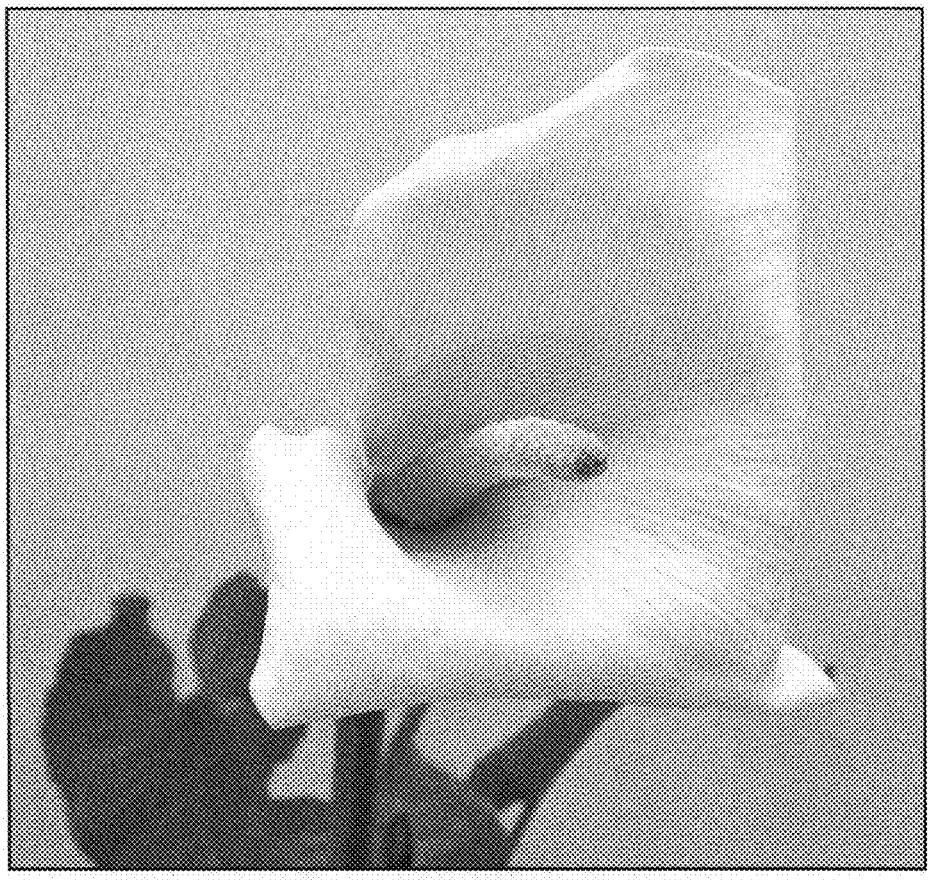
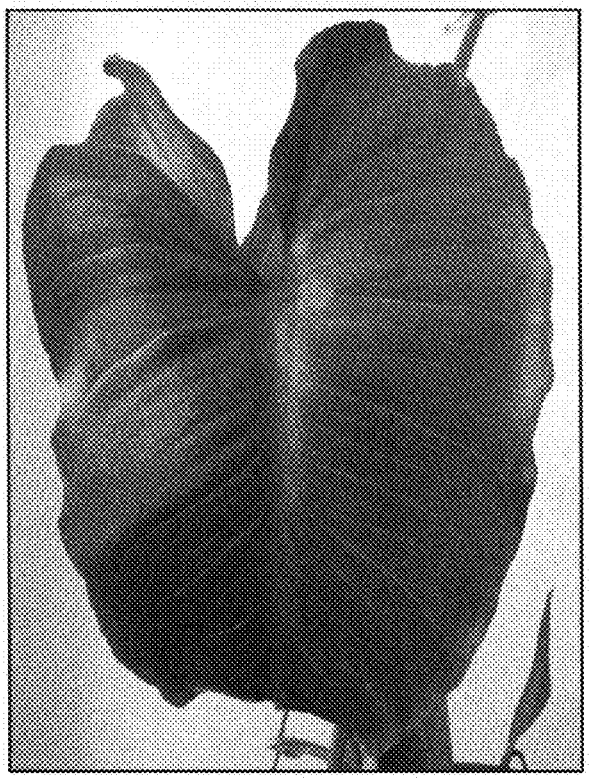

* * * * *